(12) United States Patent
Turunen et al.

(10) Patent No.: US 10,858,673 B2
(45) Date of Patent: Dec. 8, 2020

(54) METHOD AND AN APPARATUS FOR TREATING PLANT BASED RAW MATERIAL WITH AN ENZYMATIC HYDROLYSIS

(71) Applicant: UPM-KYMMENE CORPORATION, Helsinki (FI)

(72) Inventors: Sami Turunen, Lappeenranta (FI); Juha Tamper, Levänen (FI)

(73) Assignee: UPM KYMMENE CORPORATION, Helsinki (FI)

( * ) Notice: Subject to any disclaimer, the term of this patent is extended or adjusted under 35 U.S.C. 154(b) by 444 days.

(21) Appl. No.: 15/545,988

(22) PCT Filed: Feb. 5, 2016

(86) PCT No.: PCT/FI2016/050075
§ 371 (c)(1),
(2) Date: Jul. 24, 2017

(87) PCT Pub. No.: WO2016/124821
PCT Pub. Date: Aug. 11, 2016

(65) Prior Publication Data
US 2018/0340192 A1 Nov. 29, 2018

(30) Foreign Application Priority Data
Feb. 6, 2015 (FI) .................................... 20155076

(51) Int. Cl.
| | |
|---|---|
| *C12P 7/10* | (2006.01) |
| *C12P 19/02* | (2006.01) |
| *C12M 1/00* | (2006.01) |
| *C08H 7/00* | (2011.01) |
| *C08H 8/00* | (2010.01) |
| *C12M 1/33* | (2006.01) |
| *C13K 13/00* | (2006.01) |
| *C12N 1/18* | (2006.01) |

(52) U.S. Cl.
CPC ................. *C12P 7/10* (2013.01); *C08H 6/00* (2013.01); *C08H 8/00* (2013.01); *C12M 45/02* (2013.01); *C12M 45/09* (2013.01); *C12M 45/20* (2013.01); *C12N 1/18* (2013.01); *C12P 19/02* (2013.01); *C13K 13/007* (2013.01); *C12P 2201/00* (2013.01)

(58) Field of Classification Search
None
See application file for complete search history.

(56) References Cited

U.S. PATENT DOCUMENTS

2012/0193049 A1   8/2012   Yu
2015/0041083 A1   2/2015   Yoshikawa

FOREIGN PATENT DOCUMENTS

| CN | 101362029 A | 2/2009 | |
|---|---|---|---|
| CN | 101743257 A | 6/2010 | |
| CN | 102115994 A | 7/2011 | |
| CN | 103998617 A | 8/2014 | |
| EP | 2336194 A1 | 6/2011 | |
| RU | 2476581 C2 | 9/2011 | |
| WO | WO 2008/131229 A1 | 10/2008 | |
| WO | 2009080737 A2 | 7/2009 | |
| WO | WO-2009080737 A2 * | 7/2009 | ............... C12P 7/10 |
| WO | WO 2014/009604 | 1/2014 | |
| WO | 2014068196 A2 | 5/2014 | |

OTHER PUBLICATIONS

Brownell, H.H. et al., Biotechnol. Bioeng. 1986, vol. 28, pp. 792-801.*
Sievers et al., "Performance and techno-economic assessment of several solid-liquid separation technologies for processing dilute-acid pretreated corn stover", Bioresource Technology, 2014, vol. 167, pp. 291-296.
Reyes, et al, "Fractionation of P. radiata wood chips by autohydrolysis and steam explosion processes", 3rd Symposium on Biotechnology Applied to Lignocelluloses, Oct. 26-29, 2014.
Moxley, "Auto Hydrolysis and steam explosion", Novozymes Presentation Paper, 2011, pp. 1-9.
Jacquet et al., "Application of steam explosion as pretreatment on lignocellulosic material: A review", Industrial & Engineering Chemistry Research, vol. 54, Feb. 4, 2015.
Li Cui et al., "Influence of steam explosion pretreatment on the composition and structure of wheat straw", Bioresouces, vol. 7, 2012, pp. 4202-4213.
Holmes et al., "Two-stage pretreatment to enable a cleaner process—insights from lab scale testing and experiences in pilot scale-up", 34th SBFC, 2012.
Hoyer et al., "Influence of fiber degradation and concentration of fermentable sugars on simultaneous saccharification and fermentation of high-solids spruce slurry to ethanol", Biotechnology for Biofuels, vol. 6, 2013, pp. 1-9.

(Continued)

*Primary Examiner* — Heidi Reese
(74) *Attorney, Agent, or Firm* — Nixon Peabody LLP

(57) ABSTRACT

The invention relates to a method and an apparatus for treating plant based raw material with an enzymatic hydrolysis, in which the plant based raw material (1) is treated to form lignocellulosic material (3a,3b) and the lignocellulosic material (3a,3b) or its fraction (10) is conducted into the enzymatic hydrolysis (4), wherein the method comprises at least one treatment stage (2a,2b,2c) in which the plant based raw material (1) is treated so that the lignocellulosic material (3a,3b) contains over 80% fine solid particles which are fiber-like or indefinable particles smaller than 0.2 mm, defined by an optical measurement device, the lignocellulosic material (3a,3b) or at least one fraction (10) of the lignocellulosic material is supplied into the enzymatic hydrolysis (4) for forming a lignin based material (5), and at least one solid-liquid separation stage (6) after the enzymatic hydrolysis (4) in which a lignin fraction (7) and a soluble carbohydrate containing fraction (8) are separated. Further, the invention relates to the soluble carbohydrate containing fraction, the lignin fraction, the lignin based material, the liquid fraction and the solid fraction, and their uses.

21 Claims, 5 Drawing Sheets

(56) References Cited

OTHER PUBLICATIONS

Kinnarinen et al., "Influence of enzyme loading on enzymatic hydrolysis of cardboard waste and size distribution of the resulting fiber residue", Bioresource Technology, vol. 159, 2014, pp. 136-142.
Dărăban et al., "Pretreatment methods to obtain pumpable high solid loading wood-water slurries for continuous hydrothermal liquefaction systems", Biomass and Bioenergy, vol. 81, Aug. 8, 2015, pp. 442-443.
International Search Report from International Application No. PCT/FI2016/050075 dated Apr. 18, 2016.
Search Report from Patent Application No. 20155076 dated Sep. 3, 2015.
Zorina N.V. et al, Nauchnoe Soobschestvo Studentov XXI Stoletiya, Tehnichie Nauki: Materialy XII Studencheskoi Mezhdynarodnoi Nauchno-Prakticheskoi Konferentsii, Novosibirsk, SibAK, pp. 27-30 (12 pages, w/English Translation).
International Search Report in International Patent Application No. PCT/FI2016/050075, completed Aug. 1, 2019 (4 pages, w/English Translation).
Chinese Office Action in Chinese Patent Application No. CN 201680009080.4, dated Apr. 2, 2020 (27 pages, w/English Translation).
Russian Acceptance Decision in Russian Patent Application No. RU 2017130702/10, dated May 28, 2020 (13 pages, w/English Translation).

* cited by examiner

METHOD AND AN APPARATUS FOR TREATING PLANT BASED RAW MATERIAL WITH AN ENZYMATIC HYDROLYSIS

CROSS-REFERENCE TO RELATED APPLICATIONS

This application is a U.S. National Stage of International Application No. PCT/FI2016/050075, filed on Feb. 5, 2016, which claims priority to Finnish Patent No. 20155076, filed Feb. 6, 2015, the contents of each of which are incorporated herein by reference in their entireties.

FIELD OF THE INVENTION

The invention relates to a method and an apparatus for treating plant based raw material with an enzymatic hydrolysis. Further, the invention relates to a soluble carbohydrate containing fraction and its use. Further, the invention relates to a lignin fraction and its use.

BACKGROUND OF THE INVENTION

Known from prior art is different methods for forming carbohydrates and lignin from different raw materials, such as biomass. Many bio-refinery processes, e.g. hydrolysis, generate lignin and sugars after the treatment of the biomass.

OBJECTIVE OF THE INVENTION

The objective of the invention is to disclose a new method for producing a lignin fraction and a soluble carbohydrate containing fraction. Another objective of the invention is to produce a pure lignin fraction. Another objective of the invention is to produce a lignin fraction and soluble carbohydrate containing fraction effectively. Another objective of the invention is to improve an enzymatic hydrolysis process.

SUMMARY OF THE INVENTION

The method for treating plant based raw material with an enzymatic hydrolysis according to the present invention is characterized by what is presented in claim 1.

The apparatus for treating plant based raw material with an enzymatic hydrolysis according to the present invention is characterized by what is presented in claim 17.

The soluble carbohydrate containing fraction according to the present invention is characterized by what is presented in claim 23.

The lignin fraction according to the present invention is characterized by what is presented in claim 24.

The lignin based material according to the present invention is characterized by what is presented in claim 25.

The liquid fraction according to the present invention is characterized by what is presented in claim 26.

The solid fraction according to the present invention is characterized by what is presented in claim 27.

The use of the soluble carbohydrate containing fraction according to the present invention is characterized by what is presented in claim 28.

The use of the lignin fraction according to the present invention is characterized by what is presented in claim 29.

The use of the lignin based material according to the present invention is characterized by what is presented in claim 30.

The use of the liquid fraction according to the present invention is characterized by what is presented in claim 31.

The use of the solid fraction according to the present invention is characterized by what is presented in claim 32.

The use of the liquid mixture according to the present invention is characterized by what is presented in claim 33.

BRIEF DESCRIPTION OF THE DRAWINGS

The accompanying drawings, which are included to provide a further understanding of the invention and constitutes a part of this specification, illustrate some embodiments of the invention and together with the description help to explain the principles of the invention. In the drawings.

DETAILED DESCRIPTION OF THE INVENTION

Figure 1:
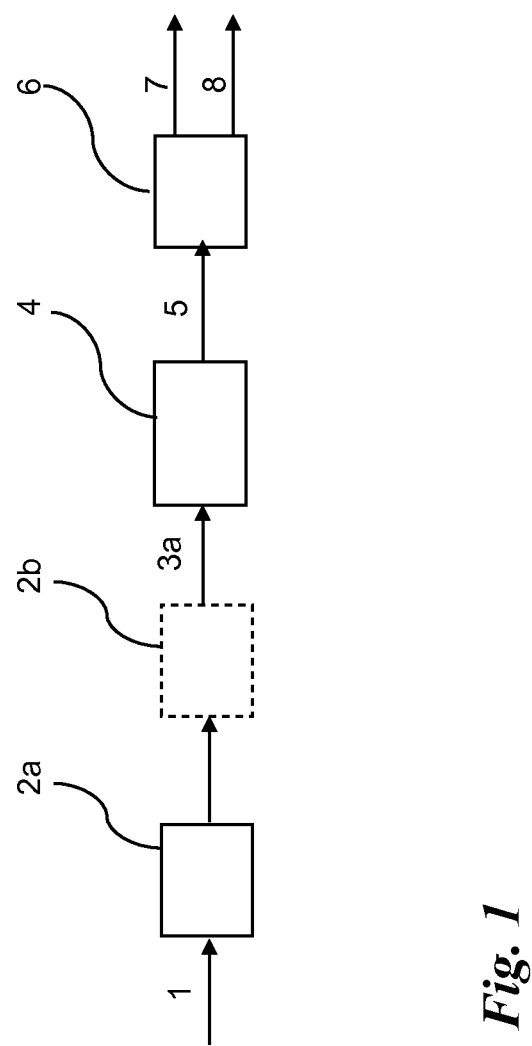
FIG. 1 is a flow chart illustration of a method according to one embodiment of the present invention.

In a method for treating plant based raw material (1) with an enzymatic hydrolysis (4), the plant based raw material (1) is treated to form lignocellulosic material (3a,3b), and the lignocellulosic material (3a,3b) or its fraction (10) is conducted into the enzymatic hydrolysis (4). The method comprises at least one treatment stage (2a,2b,2c) in which the plant based raw material (1) is treated so that the lignocellulosic material (3a,3b) contains over 80% fine solid particles which are fiber-like or indefinable particles smaller than 0.2 mm, defined by an optical measurement device, e.g. by Metso FS5, and the lignocellulosic material (3a,3b) or at least one fraction (10) of the lignocellulosic material is supplied into the enzymatic hydrolysis (4) for forming a lignin based material (5). Further, the method comprises at least one solid-liquid separation stage (6) after the enzymatic hydrolysis (4) into which the lignin based material (5) is supplied and in which a lignin fraction (7) and a soluble carbohydrate containing fraction (8) are separated.

Figure 2:
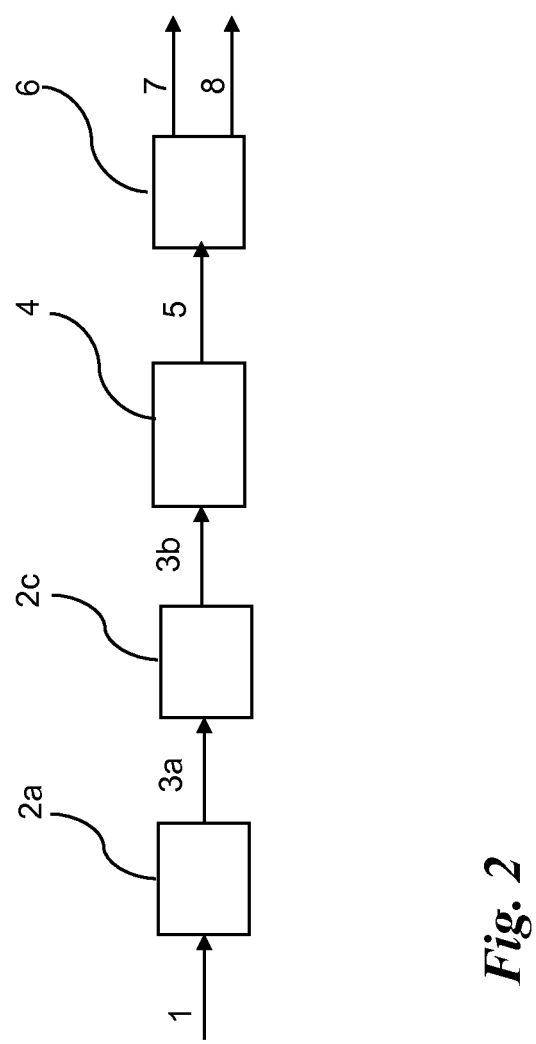
FIG. 2 is a flow chart illustration of a method according to another embodiment of the present invention.
Figure 3:
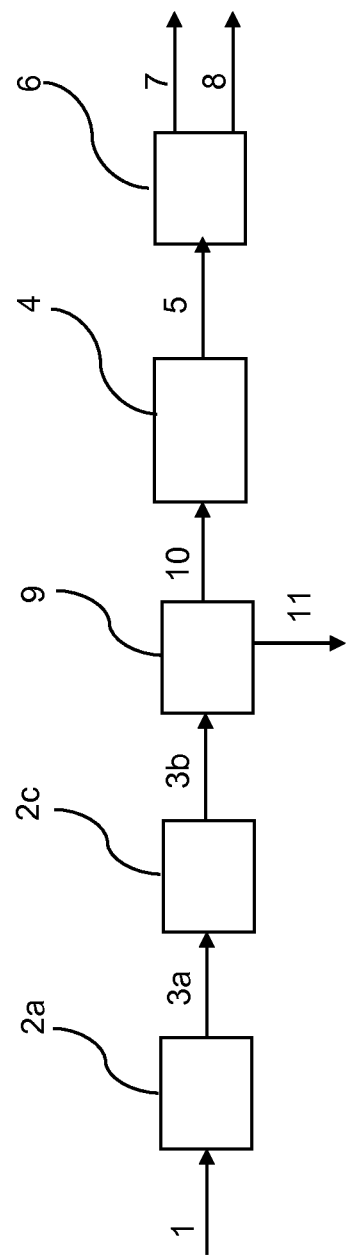
FIG. 3 is a flow chart illustration of a method according to another embodiment of the present invention.
Figure 4:
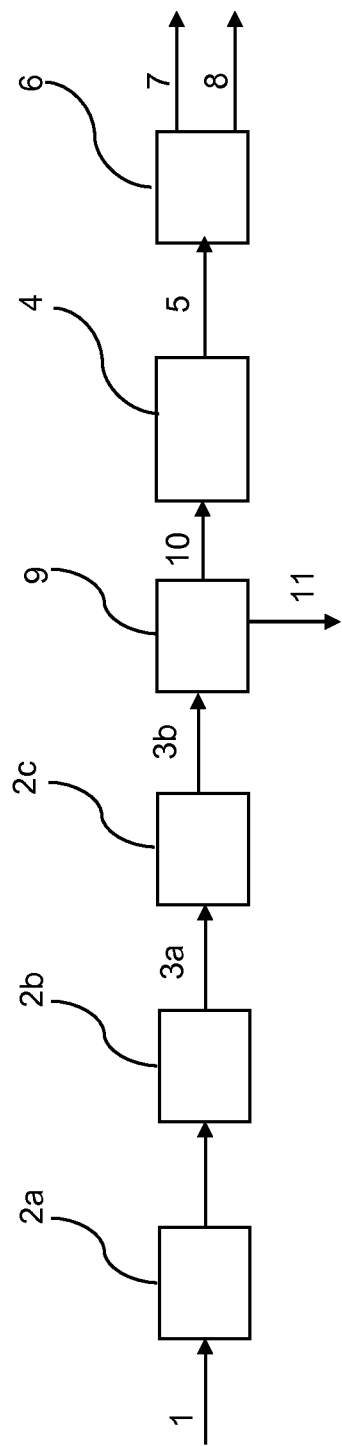
FIG. 4 is a flow chart illustration of a method according to another embodiment of the present invention.

One embodiment of the method of the present invention is shown in FIG. 1. Another embodiment of the method of the present invention is shown in FIG. 2. Another embodiment of the method of the present invention is shown in FIG. 3. Another embodiment of the method of the present invention is shown in FIG. 4.

The apparatus comprises at least one treatment device (2a,2b,2c) in which the plant based raw material (1) is treated to form lignocellulosic material (3a,3b) so that the lignocellulosic material (3a,3b) contains over 80% fine solid particles which are fiber-like or indefinable particles smaller than 0.2 mm, defined by an optical measurement device, e.g. by Metso FS5, at least one enzymatic hydrolysis device (4) in which a lignin based material (5) is formed from the lignocellulosic material (3a,3b) or at least one fraction (10) of the lignocellulosic material, at least one solid-liquid separation device (6) after the enzymatic hydrolysis device in which a lignin fraction (7) and a soluble carbohydrate containing fraction (8) is separated from lignin based material (5), and at least one feeding device for feeding the plant based raw material (1) into the treatment device. The feeding device can be any feeding device, e.g. pump, screw, inlet means or other suitable feeding device. Further, the apparatus can comprise means, such as discharge means or outlet means, e.g. pipe, pipe fitting or assembly, for supplying the soluble carbohydrate containing fraction and lignin fraction out from the apparatus.

In this context, an enzymatic hydrolysis means any enzymatic hydrolysis. In one embodiment, the enzyuratic hydrolysis is an enzymatic hydrolysis of cellulose.

In this context, a soluble carbohydrate containing fraction (8) means any soluble carbohydrate containing filtrate which is separated from the lignin based material (5) at the solid-liquid separation stage (6) after the enzymatic hydrolysis. In a preferred embodiment, the soluble carbohydrate containing fraction includes carbohydrates, preferably C6 sugars ($C_6H_{12}O_6$ or $C_6(H_2O)_n$). The soluble carbohydrate containing fraction may comprise carbohydrates, such as monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or ($C_5H_8O_4)_n$). Preferably, the soluble carbohydrate containing fraction comprises soluble C6 carbohydrates ($C_6H_{12}O_6$ or $C_6(H_2O)_n$) and other soluble carbohydrates. The soluble carbohydrate containing fraction may comprise also other components.

In this context, a lignin fraction (7) means a solid residue, such as a solid cake, when the soluble carbohydrate containing filtrate has been separated from the lignin based material (5) at the solid-liquid separation stage (6) after the enzymatic hydrolysis. In a preferred embodiment, the lignin fraction comprises lignin and carbohydrates, preferably solid C6 carbohydrates ($C_6H_{12}O_6$ or $C_6(H_2O)_n$). The lignin fraction may comprise also other carbohydrates and other components. Preferably, the lignin fraction is in the solid form.

In this context, lignin based material (5) means any lignin containing composition that can be in the form of slurry. The lignin based material contains soluble compounds, solid material and liquid, e.g. water. In one embodiment, the lignin based material contains at least soluble carbohydrates and lignin. In one embodiment, the lignin based material may comprise also other solid carbohydrates and/or other components. In one embodiment, the lignin based material can be pumped. In one embodiment, the lignin based material contains free liquid, such as free water. Preferably, the lignin based material has been formed from the lignocellulosic material (3a,3b), in one embodiment from solid fraction (10) of the lignocellulosic material (3a,3b). In one embodiment, the lignin based material is a crude lignin slurry.

In this context, plant based raw material (1) means any plant based raw material, e.g. wood based raw material and/or other plant based material. The plant based raw material includes lignin, cellulose and hemicellulose. In one embodiment, the plant based raw material is selected from the group consisting of wood based material, wood, lignocellulosic biomass, agricultural residues, bagasse based material, sugarcane bagasse, corn based material, corn stover, wheat straw, rice straw, woody biomass, woody perennials, vascular plants and the like and their mixtures and their combinations. In one embodiment, the plant based raw material comprises is wood based material or a mixture comprising wood based material. In one embodiment, the plant based raw material is wood based material or a mixture comprising wood based material. In one embodiment, the wood based material is selected from hardwood, softwood or their combination. In one embodiment, the plant based raw material comprises plant pieces, e.g. wood pieces.

In this context, lignocellulosic material (3a,3b) refers any lignocellulosic material which has been formed by treating, e.g. pretreating, from the plant based raw material by means of at least one suitable treatment method in one or more steps. In one embodiment, the lignocellulosic material contains carbohydrates and lignin. Preferably, the carbohydrates have $C_n(H_2O)_n$ or $C_n(H_2O)_{n-1}$. The carbohydrates can comprise monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or ($C_5H_8O_4)_n$). Preferably, the lignocellulosic material includes carbohydrates, such as soluble C5 carbohydrates ($C_5H_{10}O_5$ or $C_5(H_2O)_n$) and solid C6 carbohydrates ($C_6H_{12}O_6$ or $C_6(H_2O)_n$). The lignocellulosic material may contain one or more lignocellulosic material components. In one embodiment, the lignocellulosic material is in the form of suspension which contains liquid, such as water.

The lignocellulosic material (3a,3b) is formed from the plant based raw material (1) and is treated at the treatment stage, preferably in one or more treatment step (2a,2b,2c). In one embodiment, the treatment stage comprises at least one pretreatment step (2a,2b) which is selected from the group consisting of physical treatment, such as milling, extrusion, microwave treatment, ultrasound treatment and freeze treatment, chemical treatment, such as acid treatment, alkaline treatment, ionic liquid treatment, organosolv treatment and ozonolysis, physico-chemical treatment, such as steam explosion treatment, ammonia fiber explosion treatment, $CO_2$ explosion treatment, liquid hot water treatment and wet oxidation, biological treatment and their combinations. Preferably, the plant based raw material is treated to dissolve hemicellulose. In one embodiment, the lignocellulosic material is formed or treated by the hydrolysis, e.g. acid hydrolysis, autohydrolysis, thermal hydrolysis, enzymatic hydrolysis, supercritical hydrolysis and/or subcritical hydrolysis, in which at least a part of lignin is separated from the raw material in connection with the hydrolysis. In one embodiment, the lignocellulosic material is formed or treated by the steam explosion, in which hemicelluloses are treated and in which at least a part of polysaccharides of the hemicelluloses degrade into monosaccharides and oligosaccharides by means of a hydrolysis and in which pressure is rapidly released. In one embodiment, the lignocellulosic material is formed or treated by the hydrolysis and by the steam explosion in one or more steps. In one embodiment, the lignocellulosic material is formed or treated by the catalytic pretreatment, e.g. by using acid or base as catalyst. In the pretreatment process the plant based raw material enters the reactor unit where the pretreatment takes place. The lignocellulosic material can be treated by means of one or more pretreatment. In one embodiment, the treated lignocellulosic material can be blown to a blowtank. In one embodiment, the lignocellulosic material can be dewatered, e.g. by dewatering presses in two stages. The dewatering makes possible to separate sugar based streams.

In one embodiment, the plant based raw material (1) is treated by means of a steam explosion treatment at the pretreatment step (2a,2b). In one embodiment, the plant based raw material (1) is treated by means of a steam explosion treatment in presence of a chemical agent at the pretreatment step. In one embodiment, the chemical agent is a non-alkaline agent. In one embodiment, the chemical agent is an acid. In one embodiment, the chemical agent is a dilute acid, e.g. $H_2SO_4$. In one embodiment, the chemical agent is $H_2SO_4$. In one embodiment, the chemical agent may be any dilute acid. In one embodiment, pH of the dilute acid is between 1.5-2.5. In one embodiment, temperature is under 180° C. in the steam explosion if water is used as a single solvent. In one embodiment, temperature is between 170-210° C. in the steam explosion if water is used as a single solvent. In one embodiment, temperature is 130° C. or over 130° C. in the steam explosion if ethanol is used as a solvent. In one embodiment, pressure is depending on temperature in the steam explosion. In one embodiment, pressure is between 8-20 bar in the steam explosion, especially if water is used as a single solvent. In one embodiment, pH is between 1-4, in one embodiment 1-3, in one embodiment 1-2, in connection with the steam explosion. In one embodiment, pH is between 1-4, in one embodiment 1-3, in one embodiment 1-2, in the hydrolysis in connection with the steam explosion. In one embodiment, the apparatus comprises a means for a steam explosion. By means of the dilute acid treatment and the steam explosion the most of the polysaccharides of the hemicelluloses degrade into monosaccharides, and partly into oligosaccharides, and almost all of hemicellulose can be hydrolyzed by short residence time at typical conditions.

In one embodiment, the plant based raw material (1) is treated by means of a hydrolysis and a mechanical treatment at the pretreatment steps (2a,2b).

In one embodiment, the lignocellulosic material (3a) is treated by means of a soaking (2c) after the pretreatment step (2a,2b). In one embodiment, the lignocellulosic material (3a) is diluted for the soaking (2c), e.g. before and/or during the soaking. In one embodiment, the dry matter content of the lignocellulosic material (3a) is adjusted for the soaking, e.g. before and/or during the soaking, so that the lignocellulosic material comprises over 40% by weight liquid, in one embodiment over 50% by weight liquid, in one embodiment over 60% by weight liquid, and in one embodiment over 70% by weight liquid. In one embodiment, temperature is between 20-100° C., in one embodiment 20-90° C., in one embodiment 50-90° C., in one embodiment 50-80° C., in the soaking. In one embodiment, the residence time is below 72 hours, in one embodiment below 24 hours. In one embodiment, the residence time is below 12 hours, in one embodiment below 6 hours, in one embodiment below 3 hours, and in one embodiment below 2 hours. In one embodiment, the residence time is over 15 min, in one embodiment over 30 min, and in one embodiment over 45 min. In one embodiment, the apparatus comprises a soaking device. By means of the soaking good recovery of the hemicellulose can be achieved.

In one embodiment, the lignocellulosic material (3a,3b) or its solid fraction (10), preferably material which is supplied to the enzymatic hydrolysis (4), consists of fine solid particles. Particle size of the lignocellulosic material or its solid fraction can be measured with an optical measurement device, such as Metso FS5 or Coulter LS230. In one embodiment, the lignocellulosic material (3a,3b) or its solid fraction (10) contains over 85%, in one embodiment over 90%, in one embodiment over 92%, and in one embodiment over 94%, fine solid particles, defined by an optical measurement device, such as by Metso FS5. The fine solid particles can be fiber-like or indefinable particles smaller than 0.2 mm. In one embodiment, the lignocellulosic material (3a,3b) or its solid fraction (10) contains fine solid particles from which over 85%, in one embodiment over 90%, in one embodiment over 92%, and in one embodiment over 94%, are smaller than 0.2 mm, defined by Metso FS5. In one embodiment, the lignocellulosic material (3a,3b) or its solid fraction (10) contains fine solid particles which are particles that are small enough to pass through the Bauer McNett 200-mesh screen. In one embodiment, the lignocellulosic material (3a,3b) or its solid fraction (10) comprises fine solid particles which have particle size Mode between 18-300 μm, defined by Coulter LS230. In one embodiment, the lignocellulosic material (3a,3b) or its solid fraction (10) comprises fine solid particles which have Coulter LS Particle size Mode 19-200 μm, in one embodiment 20-150 μm, in one embodiment 20-120 μm, and in one embodiment 21-75 μm, defined by Coulter LS230. The values for particle size are depending on the method and thus values from Metso FS5 and Coulter LS230 and Bauer McNett cannot be directly compared. Particle size of the solid particles can be defined based on ISO 16065-N or TAPPI T271. The pretreatment process decreases the particle size and fibre length of original wood fibre, which can be defined by separating fibres by cooking the wood in e.g. sulphate process or maceration. The sulphate process is resulting fibre length of about 80% of the one after the maceration.

In one embodiment, the viscosity of the lignocellulosic material (3a,3b) or its fraction (10), preferably material which is supplied to the enzymatic hydrolysis (4), is below 18000 mPas, in one embodiment below 13000 mPas, in one embodiment below 10000 mPas, and in one embodiment below 8000 mPas, at 15% dry matter content, measured by Brookfield viscosity device at 45° C. with 10 rpm and spindel type "Vane". In this context, the lignocellulosic material or its fraction comprises below 20 w-% soluble matter during the viscosity measurement. By means of the suitable viscosity the separation and the enzymatic hydrolysis can be improved.

In one embodiment, the lignocellulosic material (3a,3b) or its solid fraction (10) contains over 80% fine solid particles which are fiber-like or indefinable particles smaller than 0.2 mm, defined by an optical measurement device, e.g. by Metso FS5, and the viscosity of the lignocellulosic material (3a,3b) or its fraction (10) is below 18000 mPas at 15% dry matter content, measured by Brookfield viscosity device at 45° C. with 10 rpm and spindel type "Vane". In one embodiment, the lignocellulosic material (3a,3b) or its solid fraction (10) comprises fine solid particles which have particle size Mode between 18-300 μm, defined by Coulter LS230, and the viscosity of the lignocellulosic material (3a,3b) or its fraction (10) is below 18000 mPas at 15% dry matter content, measured by Brookfield viscosity device at 45° C. with 10 rpm and spindel type "Vane". In one embodiment, the viscosity of the lignocellulosic material (3a,3b) or its fraction (10) is below 18000 mPas, in one embodiment below 13000 mPas, in one embodiment below 10000 mPas, and in one embodiment below 8000 mPas, at 15% dry matter content, measured by Brookfield viscosity device at 45° C. with 10 rpm and spindel type "Vane". In one embodiment, the lignocellulosic material (3a,3b) or its solid fraction (10) contains over 85%, in one embodiment over 90%, in one embodiment over 92%, and in one embodiment over 94%, fine solid particles which are fiber-like or indefinable particles smaller than 0.2 mm, defined by Metso FS5. In one embodiment, the lignocellulosic material (3a, 3b) or its solid fraction (10) comprises fine solid particles which have Particle size Mode 19-200 μm, in one embodiment 20-150 μm, in one embodiment 20-120 μm, and in one embodiment 21-75 μm, defined by Coulter LS230.

In one embodiment, dry matter content of the lignocellulosic material (3a,3b) is 20-80% by weight, in one embodiment 30-70% by weight, in one embodiment 50-60% by weight, after the pretreatment (2,2b) and/or soaking (2c). The dry matter content is determined at 45° C. by means of evaporating. When the determination of the dry matter content is made at temperature 45° C. so also small-molecular organic compounds remain in the mass during the drying of the determination. In one embodiment, the determination of the dry matter content may be done so that it is based, at least partly or as applied, on NREL (National renewable energy laboratory) Laboratory Analytical Procedures for standard biomass analysis determined in the Technical Report NREL/TR-510-48087 (revised July 2011).

In one embodiment, the lignocellulosic material (3a,3b) is diluted with liquid, preferably with water or a filtrate from a separation, or steam to form the feed to the separation stage (9) or the enzymatic hydrolysis (4). In one embodiment, feed concentration of the lignocellulosic material (3a,3b) is 2-60% by weight, in one embodiment 5-30% by weight, in one embodiment 10-20% by weight. If feed concentration of the lignocellulosic material is low so then size of the device increases, for example at the separation stage (9).

In one embodiment, pH is adjusted before the enzymatic hydrolysis (4). In one embodiment, the pH is between 4.0-6.0. Preferably, pH value depends on an enzyme.

In one embodiment, the lignocellulosic material (3a,3b) is conducted a solid-liquid separation stage (9) in which a liquid fraction (11) and a solid fraction (10) are separated before the enzymatic hydrolysis, and the solid fraction (10), in one embodiment at least a part of the solid fraction (10), is conducted into the enzymatic hydrolysis (4). The apparatus comprises at least one solid-liquid separation device for separating a liquid fraction (11) and a solid fraction (10). In one embodiment, a washing filtrate or liquid fraction or a part of the liquid fraction from the separation stage (9) is recirculated to the lignocellulosic material (3a) for the soaking (2c), e.g. before and/or during the soaking, and/or to the lignocellulosic material (3b) before the solid-liquid separation stage (9) in order to dilute the lignocellulosic material.

The separation stage (9) before the enzymatic hydrolysis may be carried out by means of a similar separation method or device as used in the separation stage (6) after the enzymatic hydrolysis or by means of other suitable separation method or device.

In this context, a liquid fraction (11) means any liquid fraction which is separated from the lignocellulosic material (3a,3b) at any solid-liquid separation stage (9) before the enzymatic hydrolysis. In a preferred embodiment, the liquid fraction includes carbohydrates, preferably C5 sugars ($C_5H_{10}O_5$ or $(C_5(H_2O))_n$). The liquid fraction may be comprise carbohydrates, such as monosaccharides ($C_6H_{12}O_6$ or $C_5H_{10}O_5$), disaccharides ($C_{12}H_{22}O_{11}$), oligosaccharides and/or polysaccharides ($((C_6H_{10}O_5)_n$ or $(C_5H_8O_4)_n$). Preferably, the liquid fraction comprises soluble C5 carbohydrates ($C_5H_{10}O_5$ or $C_5(H_2O)_n$) and other carbohydrates. The liquid fraction may comprise also other components.

In this context, a solid fraction (10) means any solid fraction which is separated from the lignocellulosic material (3a,3b) at any solid-liquid separation stage (9) before the enzymatic hydrolysis. In a preferred embodiment, the solid fraction comprises carbohydrates, and preferably solid C6 carbohydrates ($C_6H_{12}O_6$ or $C_6(H_2O)_n$), and lignin. The solid fraction may comprise also other carbohydrates and other components.

The solid-liquid separation stage (6,9) may comprise one or more separation steps. In one embodiment, the solid-liquid separation is carried out in one or more separation steps in the separation stage. In one embodiment, the solid-liquid separation stage comprises more than one sequential separation steps. In one embodiment, the solid-liquid separation stage comprises different procedures which may be done in separate separation steps. Alternatively, more than one procedure is done in one process step.

In one embodiment, the method comprises more than one separation stages (6,9). In one embodiment, the method comprises more than one sequential separation stages. In one embodiment, the apparatus comprises more than one separation devices. In one embodiment, the solid-liquid separation stage comprises at least one separation device. In one embodiment, the solid-liquid separation stage comprises more than one separation device. In one embodiment, one or more separation steps can be done in the same separation device. In one embodiment, the separation device comprises one or more separation step, e.g. separation segment.

In one embodiment, the separation device is based on a countercurrent washing. In one embodiment, the separation device is selected from the group consisting of filtration device, centrifugal device and their combinations. In one embodiment, the separation device is selected from the group consisting of pressure filtration device, vacuum filtration device, filtration device based on underpressure, filtration device based on overpressure, filter press, other suitable press, centrifugal device and their combinations. In one embodiment, the separation device is a pressure filtration device, vacuum filtration device, filtration device based on underpressure or filtration device based on overpressure. Alternatively, the separation device can be another washing device in which low amount of washing water is used and washing is done in high dry matter content. Then good recovery can be achieved.

In one embodiment, the separation is based on filtration, centrifugal treatment or their combination. In one embodiment, the filtration is carried out by pressure, underpressure or overpressure.

In one embodiment, the solid-liquid separation stage (6,9) comprises a filtration in which the soluble carbohydrate containing fraction or liquid fraction is separated in a liquid form and a solid cake is formed. Preferably, pressure is used in the filtration. In one embodiment, liquid is separated by a pressure difference, such as by means of vacuum or overpressure. In one embodiment, the solid-liquid separation stage comprises a washing in which a displacement washing of the lignocellulosic material is carried out with small amount clean water in order to remove majority of sugars, inhibitors and other soluble compounds from the solid lignocellulosic material and to provide high recovery of soluble compounds. Preferably, ratio of washing water to solid is below 6, preferably below 3 and more preferably below 1.5. In one embodiment, the solid-liquid separation stage comprises the filtration and washing. In one embodiment, the filtration and washing is carried out in a static chamber, preferably in a non-moving chamber. In one embodiment, the filtration and washing is carried out in one device under pressure without mixing between the filtration and washing. Preferably, said separation device comprising the filtration and washing is in the vertical or horizontal plane, not in the inclined plane. High concentration and recovery of soluble material in the liquid phase can be achieved with small amount of clean water, and a solid fraction without soluble compounds can be achieved.

In one embodiment, the separation is made by means of pressure filtration. In one embodiment, the apparatus comprises at least one pressure filtration device as the solid-liquid separation device. In one embodiment, the solid-liquid separation stage comprises one pressure filtration device. In one embodiment, the solid-liquid separation stage comprises more than one pressure filtration device. In a preferred embodiment, the washing in the pressure filtration device is based on a displacement of liquid. In one embodiment, the pressure filtration comprises a pumping step, pressing, washing step, pressing and removal of a cake. In the pumping step, the solid cake is formed and pressed. Preferably, in the pumping step, a chamber of the pressure filtration device is filled, and prepressing is made. In one embodiment, air blow is made after the pumping step or after the first pressing step to further remove liquid from the cake. Preferably, the soluble carbohydrate containing fraction or liquid fraction is separated in connection with the pumping step. In the washing step, washing water is pressed through the cake and the cake is pressed and preferably dewatered. In the washing step, the liquid of the cake can be displaced by water. In one embodiment, air blow is made in the washing step to further remove liquid from the cake. The washing filtrate is separated by pressing in connection with the washing step. The dewatered solid cake is removed from the pressure filtrate device. Preferably, the dewatered solid cake forms a solid fraction or lignin fraction. An advantage of the pressure filtration is that all separation steps can be carried out by one device.

In different separation stages the separation can be carried out by means of similar or different separation methods or separation devices.

In one embodiment, the lignin based material is diluted with liquid, preferably with water, or steam to form the feed to the separation stage (6). In one embodiment, feed concentration of the lignin based material (5) is 2-60% by weight, preferably 5-40% by weight, more preferable 10-30% by weight, into the solid-liquid separation stage (6). If feed concentration of the lignin based material is low so then size of the device increases. In one embodiment, the washing filtrate which is recovered may be used in a dilution of the lignin based material.

In one embodiment, the lignocellulosic material (3a,3b) or its fraction (10) or lignin based material (5) is fed by means of a pump, e.g. a mono pump or piston pump or other suitable pump, or other suitable feeding device into the solid-liquid separation stage (9,6). Selection of the pump or feeding device is based on e.g. feed concentration and/or viscosity of the lignocellulosic material or lignin based material.

Preferably, at least a part of the soluble carbohydrate containing fraction (8) is supplied out from the separation stage (6) after the enzymatic hydrolysis. The soluble carbohydrate containing fraction can be supplied out after any desired step of the separation stage. In one embodiment, the soluble carbohydrate containing fraction is supplied out after one or more step of the separation stage. The soluble carbohydrate containing fractions may be combined or used separately as component.

Preferably, a lignin fraction (7) comprising solids is supplied out from the solid-liquid separation stage (6) after the enzymatic hydrolysis. In one embodiment, the lignin fraction is supplied out after one or more step of the separation stage, preferably in one step. In one embodiment, the lignin fraction is supplied out after the last step.

In one embodiment, at least a part of the liquid fraction (11) is supplied out from the separation stage (9) before the enzymatic hydrolysis. The liquid fraction can be supplied out after any desired step of the separation stage. In one embodiment, the liquid fraction is supplied out after one or more step of the separation stage. The liquid fractions may be combined or used separately as component. In one embodiment, a part of the liquid fraction is separated from the lignocellulosic material (3a,3b) in connection with the treatment stage (2a,2b,2c) in which the lignocellulosic material is formed and/or treated. In one embodiment, at least a part of the liquid fraction (11) is recirculated to the lignocellulosic material (3a,3b) before the separation stage (9) or for the soaking (2c), e.g. before and/or during the soaking. An amount of fresh water can be decreased by means of the recirculation.

In one embodiment, a solid fraction (10) comprising solids is supplied out from the solid-liquid separation stage (9) and is supplied into the enzymatic hydrolysis (4). In one embodiment, the solid fraction comprises C6 carbohydrates, such as $(C_6H_{12}O_6$ or $(C_6(H_2O)_n)$, other solid carbohydrates and lignin, and some other compounds, such as some residual soluble material. In one embodiment, the solid fraction is in the form of a cake. In one embodiment, dry matter content of the cake is 30-70% by weight, preferably 35-60% by weight, more preferably 50-60% by weight, after the solid-liquid separation stage (9). In one embodiment, dry matter content of the cake is 7-70% by weight, preferably 15-45% by weight, more preferably 25-35% by weight, after the solid-liquid separation stage (9). In one embodiment, the solid fraction contains soluble compounds below 20%, preferably below 15%, more preferably below 6% by weight, most preferably below 3% by weight, after the solid-liquid separation stage (9), determined by a gravimetric washing method.

In one embodiment, the soluble carbohydrate containing fraction (8) is formed from the lignin based material (5). In one embodiment, the soluble carbohydrate containing fraction can be used as component in manufacturing a final product or can be treated or concentrated. In one embodiment, the soluble carbohydrate containing fraction (8) comprises soluble C6 carbohydrates, such as $C_6H_{12}O_6$ or $C_6(H_2O)_n$, and other soluble carbohydrates, lignin and some other compounds. The soluble carbohydrate containing fraction may contain also C5 carbohydrates. Preferably, the soluble carbohydrate containing fraction can contain monosaccharides, and oligosaccharides. Further, the soluble carbohydrate containing fraction can contain also polysaccharides. In one embodiment, the soluble carbohydrate containing fraction contains galactose, glucose, mannose, arabinose, xylose, glucuronic acid and galacturonic acid. In one embodiment, the soluble carbohydrate containing fraction contains glucose more than xylose. Total carbohydrate content can be measured with HPLC after acid hydrolysis according to standard SCAN-CM 71:09. Monomeric carbohydrate content can be measured with HPLC from liquid composition directly without acid hydrolysis. In one embodiment, the total soluble concentrate of the soluble carbohydrate containing fraction is between 20 to 280 g/l, preferably between 40 to 240 g/l, more preferable between 55 to 210 g/l after the solid-liquid separation. In one embodiment, the total soluble concentrate of the soluble carbohydrate containing fraction is between 10 to 210 g/l, preferably between to 180 g/l, more preferable between 30 to 140 g/l after the solid-liquid separation (6). In one embodiment, the total soluble concentrate of the soluble carbohydrate containing fraction is between 30 to 230 g/l, preferably between 50 to 220 g/l, more preferable between 100 to 210 g/l after the solid-liquid separation. Preferably, the soluble carbohydrate containing fraction is in the form of solution. In one embodiment, carbohydrate concentrate of the soluble carbohydrate containing fraction (8) is between 20 to 200 g/l, preferably between 40 to 170 g/l, more preferable between 50 to 150 g/l after the solid-liquid separation (6). In one embodiment, carbohydrate concentrate of the soluble carbohydrate containing fraction is between 10 to 150 g/l, preferably between 20 to 125 g/l, more preferable between 30 to 100 g/l after the solid-liquid separation. In one embodiment, carbohydrate concentrate of the soluble carbohydrate containing fraction is between 25 to 230 g/l, preferably between 50 to 215 g/l, more preferable between 100 to 200 g/l after the solid-liquid separation.

In one embodiment, the lignin fraction (7) comprising solids is formed from the lignin based material (5). In one embodiment, the lignin fraction can be used as component in manufacturing a final product or can be treated. In one embodiment, the lignin fraction (7) comprises lignin and solid C6 carbohydrates, such as ($C_6H_{12}O_6$ or ($C_6(H_2O)_n$), other solid carbohydrates and other solid components, and some other compounds, such as some residual soluble material. In one embodiment, the lignin fraction is in the form of a cake. In one embodiment, dry matter content of the lignin fraction is 20-80% by weight. In one embodiment, dry matter content of the lignin fraction is 30-60% by weight, preferably 40-60% by weight, more preferably 45-55% by weight, after the solid-liquid separation stage (6). In one embodiment, dry matter content of the lignin fraction is 7-70% by weight, preferably 15-45% by weight, more preferably 30-40% by weight, after the solid-liquid separation stage (6). The dry matter content is determined at 60° C. by means of evaporating. In one embodiment, the determination of the dry matter content may be done so that it is based, at least partly or as applied, on NREL (National renewable energy laboratory) Laboratory Analytical Procedures for standard biomass analysis determined in the Technical Report NREL/TR-510-48087 (revised July 2011). In one embodiment, the cellulose content, i.e. glucan content, of the lignin fraction (7) is 3-70% by weight, preferably 5-60% by weight and more preferably 10-60% by weight, analyzed as glucose. In this context, glucan means β-glucan, such as β-1,4-glucan, i.e. cellulose. In one embodiment, the carbohydrate content of the lignin fraction (7) is between 2 to 50% by weight. In one embodiment, the carbohydrate content is 10-30% by weight, and more preferably 15-25% by weight. In one embodiment, the carbohydrate content is 40-70% by weight, and more preferably 40-60% by weight. In one embodiment, the carbohydrate content is 5-80% by weight, and more preferably 40-70% by weight. In one embodiment, the lignin fraction (7) contains soluble compounds below 20% by weight, preferably below 15% by weight, more preferably below 6% by weight, most preferably below 3% by weight, after the solid-liquid separation stage (6). In one embodiment, water soluble matter is determined by a gravimetric washing method.

In one embodiment the liquid fraction (11) is formed from the lignocellulosic material (3a,3b). In one embodiment, the liquid fraction can be used as component in manufacturing a final product or can be treated or concentrated. In one embodiment, the liquid fraction (11) contains soluble C5 carbohydrates. The liquid fraction may contain also C6 carbohydrates, preferably below 20 w-%. Preferably, the liquid fraction can contain other monosaccharides, disaccharides, oligosaccharides and/or polysaccharides. In one embodiment, the liquid fraction contains galactose, glucose, mannose, arabinose, xylose, glucuronic acid and galacturonic acid. In one embodiment, the liquid fraction contains xylose more than glucose. In one embodiment, the liquid fraction contains glucose less than 20% by weight, in one embodiment less than 15% by weight, less than 10% by weight, from an amount of the xylose. In one embodiment, the liquid fraction contains less than 50% by weight glucose and more than 50% by weight xylose, from an amount of the glucose and xylose. In one embodiment, a ratio (w/w) of glucose to xylose, glucose:xylose, is less than 1. In one embodiment, the liquid fraction comprises soluble C5 carbohydrates, such as $C_5H_{10}O_5$ or $C_5(H_2O)_n$, and other carbohydrates and some other compounds. Total carbohydrate content can be measured with HPLC after acid hydrolysis according to standard SCAN-CM 71:09. Monomeric carbohydrate content can be measured with HPLC from liquid composition directly without acid hydrolysis. In one embodiment, the soluble carbohydrate concentrate of the liquid fraction is over 50 g/l, preferably over 70 g/l, more preferable over 100 g/l after the solid-liquid separation (9). In one embodiment, the soluble carbohydrate concentrate of the liquid fraction is below 250 g/l, in one embodiment below 200 g/l, in one embodiment below 150 g/l after the solid-liquid separation. In one embodiment, the soluble carbohydrate concentrate of the liquid fraction is between 15 to 280 g/l, preferably 30 to 200 g/l, more preferable 50 to 165 g/l after the solid-liquid separation. Preferably, the liquid fraction is in the form of solution. In one embodiment, water soluble matter is between 20 to 425 g/l, preferably 45 to 303 g/l, more preferable 75 to 250 g/l after the solid-liquid separation (9). Water soluble matter can be determined by means of a method described later as "gravimetric washing method".

In one embodiment, the soluble carbohydrate containing fraction (8) is recovered. The soluble carbohydrate containing fraction may be used as component in manufacturing a final product. In one embodiment, the soluble carbohydrate containing fraction can be concentrated for further use. In one embodiment, the soluble carbohydrate containing fraction is supplied to a further processing. In one embodiment, the monomerization of the soluble carbohydrate containing fraction is made before the further processing. In one embodiment, the soluble carbohydrate containing fraction is supplied to a fermentation process. In one embodiment, the soluble carbohydrate containing fraction is used as a source material in fermentation. In one embodiment, the soluble carbohydrate containing fraction is supplied to a hydrolysis process. In one embodiment, the soluble carbohydrate containing fraction is used as a source material in hydrolysis, e.g. acid hydrolysis or the like. In one embodiment, the soluble carbohydrate containing fraction is supplied to a chemical treatment. In one embodiment, the soluble carbohydrate containing fraction is used as a source material in the chemical treatment. In one embodiment, the soluble carbohydrate containing fraction is supplied to a catalytic treatment. In one embodiment, the soluble carbohydrate containing fraction is used as a source material in the catalytic treatment. In one embodiment, the soluble carbohydrate containing fraction is supplied to a polymerization process. In one embodiment, the soluble carbohydrate containing fraction is used as a source material in the polymerization process. In one embodiment, the soluble carbohydrate containing fraction is supplied to a depolymerization process. In one embodiment, the soluble carbohydrate containing fraction is used as a source material in the depolymerization process. In one embodiment, the soluble carbohydrate containing fraction is supplied to a degradation process. In one embodiment, the soluble carbohydrate containing fraction is used as a source material in the degradation process. In one embodiment, the soluble carbohydrate containing fraction is supplied to an enzymatic treatment. In one embodiment, the soluble carbohydrate containing fraction is used as a source material in the enzymatic treatment. In one embodiment, the soluble carbohydrate containing fraction is supplied to a manufacture of binder. In one embodiment, the soluble carbohydrate containing fraction is used as a source material in the manufacture of binder, e.g. wood based binder. In one embodiment, the soluble carbohydrate containing fraction is supplied to a manufacture of food. In one embodiment, the soluble carbohydrate containing fraction is used as a source material in the manufacture of food. In one embodiment, the soluble carbohydrate containing fraction is supplied to a manufacture of feed. In one embodiment, the soluble carbohydrate containing fraction is used as a source material in the manufacture of feed. The soluble carbohydrate containing fraction may be supplied directly to a fermentation, hydrolysis, chemical treatment, catalytic treatment, polymerization process, depolymerization process, degradation process, enzymatic treatment, manufacture of binder, manufacture of feed, manufacture of food, or other suitable process or their combinations, or alternatively via a suitable treatment step or an additional step, e.g. additional concentration step and/or purification step, to a fermentation, hydrolysis, chemical treatment, catalytic treatment, polymerization process, depolymerization process, degradation process, enzymatic treatment, manufacture of binder, manufacture of feed, manufacture of food or other suitable process or their combinations.

In one embodiment, a lignin fraction (7) comprising solids is recovered. The lignin fraction may be used as component in manufacturing a final product. In one embodiment, the lignin fraction can be treated, e.g. purified, for further use. In one embodiment, the lignin fraction is supplied to a further processing. In one embodiment, the lignin fraction is supplied to a hydrolysis which may be selected from the group consisting of acid hydrolysis, supercritical hydrolysis and/or subcritical hydrolysis and their combinations, or to a polymerization process or to a depolymerization process or to a degradation process or to a chemical treatment or to a manufacture of a composite material or to a manufacture of binder, e.g. wood based binder, or to a manufacture of feed or to a manufacture of food or to a combustion process or to other suitable process or their combinations. The lignin fraction may be supplied directly to a hydrolysis, polymerization process, depolymerization process, degradation process, chemical treatment, manufacture of a composite material, manufacture of binder, manufacture of feed, manufacture of food, combustion process or other suitable process or their combinations, or alternatively via a suitable treatment step or an additional step, e.g. additional concentration step and/or purification step, to a hydrolysis, polymerization process, depolymerization process, degradation process, chemical treatment manufacture of a composite material, manufacture of binder, manufacture of feed, manufacture of food, combustion process or other suitable process or their combinations.

In one embodiment, at least a part of lignin based material (5) comprising solids is recovered. The lignin based material may be used as component in manufacturing a final product. In one embodiment, the lignin based material can be treated, e.g. purified, for further use. In one embodiment, the lignin based material is supplied to a further processing. In one embodiment, the lignin based material is supplied to a hydrolysis which may be selected from the group consisting of acid hydrolysis, supercritical hydrolysis and/or subcritical hydrolysis and their combinations, or to a polymerization process or to a depolymerization process or to a degradation process or to a chemical treatment or to a manufacture of a composite material or to a manufacture of binder, e.g. wood based binder, or to a manufacture of feed or to a manufacture of food or to a combustion process or to other suitable process or their combinations. The lignin based material may be supplied directly to a hydrolysis, polymerization process, depolymerization process, degradation process, chemical treatment, manufacture of a composite material, manufacture of binder, manufacture of feed, manufacture of food, combustion process or other suitable process or their combinations, or alternatively via a suitable treatment step or an additional step, e.g. additional concentration step and/or purification step, to a hydrolysis, polymerization process, depolymerization process, degradation process, chemical treatment, manufacture of a composite material, manufacture of binder, manufacture of feed, manufacture of food, combustion process or other suitable process or their combinations.

In one embodiment, the liquid fraction (11) is recovered. The liquid fraction may be used as component in manufacturing a final product. In one embodiment, the liquid fraction can be concentrated for further use. In one embodiment, the liquid fraction is supplied to a further processing. The liquid fraction may be supplied directly to a fermentation, hydrolysis, chemical treatment, catalytic treatment, polymerization process, depolymerization process, degradation process, enzymatic process, manufacture of binder, manufacture of feed, manufacture of food or other suitable process or their combinations, or alternatively via a suitable treatment step or an additional step, e.g. additional concentration step and/or purification step, to a fermentation, hydrolysis, chemical treatment, catalytic treatment, polymerization process, depolymerization process, degradation process, enzymatic process, manufacture of binder, manufacture of feed, manufacture of food or other suitable process or their combinations.

In one embodiment, the solid fraction (10) is formed from the lignocellulosic material (3a,3b). In one embodiment, at least a part of the solid fraction can be recovered and used as component in manufacturing a final product. In one embodiment, the solid fraction is supplied to a further processing. The solid fraction may be supplied directly to a hydrolysis, polymerization process, depolymerization process, degradation process, chemical treatment, manufacture of a composite material, manufacture of binder, combustion process or other suitable process or their combinations, or alternatively via a suitable treatment step or an additional step, e.g. additional concentration step and/or purification step, to a hydrolysis, polymerization process, depolymerization process, degradation process, chemical treatment, manufacture of a composite material, manufacture of binder, combustion process or other suitable process or their combinations.

In one embodiment, the soluble carbohydrate containing fraction (8) and the liquid fraction (11) is combined partially or as a whole in order to form a liquid mixture. In one embodiment, the liquid mixture comprises 1-99 w-% soluble carbohydrate containing fraction and 1-99 w-% liquid fraction, from the total weight of the soluble carbohydrate containing fraction and liquid fraction. The liquid mixture may be used as component in manufacturing a final product. In one embodiment, the liquid mixture can be concentrated for further use. In one embodiment, the liquid mixture is supplied to a further processing. The liquid mixture may be supplied directly to a fermentation, hydrolysis, chemical treatment, catalytic treatment, polymerization process, depolymerization process, degradation process, enzymatic treatment, manufacture of binder, manufacture of feed, manufacture of food or other suitable process or their combinations, or alternatively via a suitable treatment step or an additional step, e.g. additional concentration step and/or purification step, to a fermentation, hydrolysis, chemical treatment, catalytic treatment, polymerization process, depolymerization process, degradation process, enzymatic treatment, manufacture of binder, manufacture of feed, manufacture of food or other suitable process or their combinations.

In one embodiment, water soluble matter is determined by a gravimetric washing method. The determination by the gravimetric washing method may be done as following: dry matter content (DM %) of raw material, e.g. the solid and soluble fraction, is measured at 60° C., the amount of solids remaining after heating the sample at 60° C. to constant weight is measured and dry matter content is calculated based on wet and dry weights. For washing about 10 g bone dry of the wet material under investigation is taken, weighted (exact weighed amount) and mixed with hot water (50° C.) in a vessel so that total amount is 200 g, the mixture is mixed 20 s (Bamix Mono freehand food blender, 'C' blade, speed 1 (7000 rpm)), the mixture is soaked with soaking time 5 min, the mixture is mixed 10 s (Bamix Mono freehand food blender, C' blade, speed 1 (7000 rpm)), mass of a dry filter paper is measured, the mixture is filtered by means of Büchner (dia.125 mm) and the filter paper, an inward relief valve is closed when a cake is matt (dry) in whole, a filtrate is taken and the blender and vessel is washed with the filtrate and the filtrate is filtered again through the cake, the cake is washed three times with hot water, a 100 g, so that suction effect is maintained the whole time and washing water (100 g) is added when the cake is matt (dry) in whole, a foil dish is weighed, the cake with the filter paper is dried in the foil dish, the dried cake (60° C.) with the filter paper is weighed in the foil dish and mass of the filter paper and foil dish is subtracted from mass of the dried cake, filter paper and foil dish, and then soluble matter free solid, i.e. water insoluble solids (WIS) of wet material under investigation, can be determined. Water insoluble solids, WIS %, can be calculated: WIS %=(weight of washed and dried material, e.g. the cake)/(weight of the wet slurry for washing, e.g. the raw material). Water soluble matter, WS %, of dry matter can be calculated: WS %=(dry matter (DM %) of the original slurry, e.g. the raw material)–(water insoluble solids, WIS %).

In one embodiment, with high soluble material content (25-50% of total dry matter soluble) of raw material, the lignin fraction (7) or solid fraction (10) contains soluble compounds below 20%, preferably below 15%, more preferably below 9%, most preferably below 5%, by weight after the solid-liquid separation stage (6,9), measured by gravimetric washing method. In one embodiment, with lower soluble material content (below 25% of total dry matter soluble) of raw material, the lignin fraction (7) or solid fraction (10) contains soluble compounds below 9%, preferably below 6%, more preferably below 3%, by weight after the solid-liquid separation stage (6,9), measured by gravimetric washing method.

Particle size of the solid particles can be defined, e.g. by an optical measurement device, such as Metso FS5 or Coulter LS230. In one embodiment, particle size of the solid particles can be defined based on ISO 16065-N or TAPPI T271. Fibre length of the solid particles can be defined based on ISO 16065-N, when fibres are defined as material longer than 0.2 mm. Fibre length of the solid particles can be defined based on TAPPI T271, when fibre length is 0.01 to 7.60 mm. In connection with Metso FS5, Lc means contour length, i.e. centerline fiber length, which is fiber length measured from the fibers center line from one end to another. Length-weighted Lc(l) means length-weighted fiber length which is average fiber length measured from a fiber distribution weighted according to the TAPPI T271 standards. Weight-weighted Lc(w) means weight-weighted fiber length which is likewise average fiber length measured from a fiber distribution weighted according to the TAPPI T271 standards. Arithmetic Lc(n) means arithmetic mean which is calculated from the population distribution of fibers. In this result average length is calculated from the length distribution. F1(1)% means length weighted distribution % (width>10 μm, length<0.2 mm). Fiber width is measured as integral value from the middle of the fiber to account for tapered ends.

In one embodiment, length-weighted particle length Lc(l) is below [(0.4)×(corresponding unrefined sulphate pulp fibre length)], in one embodiment below [(0.3)×(corresponding unrefined sulphate pulp fibre length)], in one embodiment below [(0.2)×(corresponding unrefined sulphate pulp fibre length)], in one embodiment below [(0.1)×(corresponding unrefined sulphate pulp fibre length)].

In one embodiment, fine particle width (fraction 0-0.2 mm) is below [(0.7)×(corresponding unrefined sulphate pulp fibre length)], in one embodiment below [(0.6)×(corresponding unrefined sulphate pulp fibre length)], in one embodiment below [(0.5)×(corresponding unrefined sulphate pulp fibre length)], in one embodiment below [(0.4)×(corresponding unrefined sulphate pulp fibre length)].

In one embodiment, the determination of particle size of the solid particles in the cake needs proper sample preparation to disperse single particles to water. For dispersing about 10 g bone dry of the wet material under investigation is taken and mixed with water (about 20° C.) in a vessel so that total amount is 200 g, the mixture is soaked with soaking time 15 min, and the mixture is mixed 60 s (Bamix Mono freehand food blender, 'C' blade, speed 1 (7000 rpm)). After that the material is ready to determination specific preparation. In one embodiment, to have more reliable picture of fine particles, shorter than 0.2 mm, measurement is done by an optical measurement device, such as Metso FS5, such way that material pass the detector only once, so it is not circulated back to detector. In one embodiment, the amount of measured dry matter in one run is 1.6 g.

In one embodiment, the fine solid particles are fiber-like or indefinable particles with longest dimension shorter than 0.2 mm measured with optical Metso FS5 (fraction F1(l) of length weighted Lc(l) measurements and calculations). In one embodiment, the lignocellulosic material (3a,3b) or solid fraction (10) of hardwood comprises particles with longest dimension shorter than 0.2 mm over 70% (F1(l)>70%), preferably over 80%, more preferably over 90% and most preferably over 95% by weight, defined by Metso FS5 (single pass run). In one embodiment, the lignocellulosic material (3a,3b) or solid fraction (10) of softwood comprises particles with longest dimension shorter than 0.2 mm over 50% (F1(l)>50%), preferably over 60%, more preferably over 70% and most preferably over 80% by weight, defined by Metso FS5 (single pass run). In one embodiment, the lignin fraction (7) comprises particles with longest dimension shorter than 0.2 mm over 70% (F1(l) >70%), preferably over 80%, more preferably over 90% and most preferably over 95% by weight, defined by Metso FS5 (single pass run).

In one embodiment, the lignocellulosic material (3a,3b) or solid fraction (10) comprises fine solid particles which are fiber-like or indefinable particles. The length weighted length Lc(l) is measured based TAPPI T271 standard includes all the particles detected and filling the requirements of measurement. TAPPI T271 defines fiber length of material to have longest dimension from 0.01 to 7.60 mm.

In one embodiment, the lignocellulosic material (3a,3b) or solid fraction (10) comprises fine solid particles which are fiber-like or indefinable particles. The length weighted length Lc(l) is measured with Metso FS5 (single pass run), where Lc(l) is including also the particles below 0.2 mm. The length weighted Lc(l)-value is 40% or less of the length of corresponding unrefined sulphate pulp fibre length, preferably 30% or less, more preferably 20% or less, most preferably 10% or less. And the width of the fine particle fraction of length weighted particles (Lc(l) fraction 0-0.2 mm) is 70% or less of width of the corresponding sulphate pulp fibre, preferably 60% or less, more preferably 50% or less, the most preferably 40% or less.

In one embodiment, the lignocellulosic material (3a,3b) or solid fraction (10) of hardwood comprises fine solid particles which are fiber-like or indefinable particles. The length weighted length Lc(l) is measured with Metso FS5 (single pass run), where Lc(l) is including also the particles below 0.2 mm. The length weighted Lc(l) fractions over 0.2 mm fibre length is 50% or less, preferably 35% or less, more preferably 20% or less, most preferably 5% or less.

In one embodiment, the lignocellulosic material (3a,3b) or solid fraction (10) of softwood comprises fine solid particles which are fiber-like or indefinable particles. The length weighted length Lc(l) of solid fraction is measured with Metso FS5 (single pass run), where Lc(l) is including also the particles below 0.2 mm. The length weighted Lc(l) fractions over 0.2 mm fibre length is 60% or less, preferably 45% or less, more preferably 30% or less, most preferably 15% or less. In one embodiment, the lignocellulosic material (3a,3b) or its solid fraction (10) contains fine solid particles which comprise less than 90%, in one embodiment less than 88%, particles with below 50 µm particle size, defined by Coulter LS230. In one embodiment, the lignocellulosic material (3a, 3b) or its solid fraction (10) contains fine solid particles which comprise 50-90%, in one embodiment 60-90%, and in one embodiment 70-90%, particles with below 50 µm particle size, defined by Coulter LS230. In one embodiment, the lignocellulosic material (3a,3b) or solid fraction (10) comprises particles with equivalent circular area diameter smaller than 50 µm over 50%, in one embodiment over 70%, and preferably below 90% by weight, defined by Coulter LS230. In one embodiment, the lignocellulosic material (3a,3b) or solid fraction (10) comprises solid particles which are fiber-like or indefinable particles measured in water solution with a laser diffraction method Coulter LS230, PIDS (Polarization Intensity Differential Scattering) including. In one embodiment, the lignocellulosic material (3a,3b) or solid fraction (10) comprises particles with Mode equivalent circular area diameter less than 300 µm, in one embodiment less than 200 µm, in one embodiment less than 100 µm, in one embodiment 50 µm, in one embodiment less than 40 µm, and in one embodiment less than 30 µm, and preferably over 18 µm, defined by Coulter LS230. Coulter LS230 is based on a laser diffraction, and it measures particle size distributions by measuring the pattern of light scattered by the constituent particles in the sample. Coulter LS230 comprises an optical module consisting of a diffraction component and PIDS (Polarization Intensity Differential Scattering) assembly. The measuring range is 0.04-2000 µm so that the measuring range is 0.4-2000 µm with the diffraction component and the measuring range is 0.04-0.4 µm with the PIDS assembly.

The method and apparatus provide the liquid fraction, solid fraction, soluble carbohydrate containing fraction and lignin fraction with good quality. Further, concentration and sugar content of the soluble carbohydrate containing fraction can be increased. Further, the recovery of the soluble carbohydrate containing fraction can be increased and more pure lignin fraction solids can be formed. The lignin fraction has also very high concentration of lignin and glucan and its hydrated products. In the method, a replacement washing is preferably used which leads to further increase of the concentration of the soluble compounds and increase purity of the lignin fraction. Further, post-treating costs of the soluble carbohydrate containing fraction can be decreased. High concentration is achieved with low energy consumption.

The present invention provides an industrially applicable, simple and affordable way of making the pure lignin fraction and further the soluble carbohydrate containing fraction. The method and apparatus are easy and simple to realize as a production process. The method and apparatus are suitable for use in the manufacture of the different lignin based fractions and sugar based fractions, and final products from different starting materials.

EXAMPLES

The invention is described in more detail by the following examples with reference to accompanying drawings.

Example 1

In this example a lignin fraction and soluble carbohydrate containing fraction are produced from plant based raw material according to a process of FIG. 1.

The lignocellulosic material (3a) is formed from plant based raw material (1) by means of one pretreatment step (2a), or alternatively by means of two pretreatment steps (2a,2b). The plant based raw material (1) can be treated by means of a hydrolysis and steam explosion treatment in presence of a chemical agent, e.g. $H_2SO_4$, at the pretreatment stage. The lignocellulosic material (3a) is conducted into an enzymatic hydrolysis (4) for forming a lignin based material (5). The lignin based material (5) is conducted into a solid-liquid separation stage (6) which comprises a separation device based on filtration or centrifugal treatment. A soluble carbohydrate containing fraction (8) and a lignin fraction (7) are separated at the solid-liquid separation stage (6). The soluble carbohydrate containing fraction (8) is recovered. A solid cake (7) containing lignin is removed from the solid-liquid separation device and recovered.

Example 2

In this example a lignin fraction and soluble carbohydrate containing fraction are produced from plant based raw material according to a process of FIG. 2.

The lignocellulosic material A (3a) is formed from plant based raw material (1) by means of a pretreatment step (2a). The plant based raw material (1) can be treated by means of a hydrolysis and steam explosion treatment in presence of a chemical agent, e.g. $H_2SO_4$, at the pretreatment stage. The lignocellulosic material A (3a) is treated by means of a soaking (2c) after the pretreatment step (2a). The lignocellulosic material B (3b) from the soaking step (2c) is conducted into an enzymatic hydrolysis (4) for forming a lignin based material (5). The lignin based material (5) is conducted into a solid-liquid separation stage (6) which comprises a separation device based on filtration or centrifugal treatment. A soluble carbohydrate containing fraction (8) and a lignin fraction (7) are separated at the solid-liquid separation stage (6). The soluble carbohydrate containing fraction (8) is recovered. A solid cake (7) containing lignin is removed from the solid-liquid separation device and recovered.

Example 3

In this example a lignin fraction and soluble carbohydrate containing fraction are produced from plant based raw material according to a process of FIG. 3.

The lignocellulosic material A (3a) is formed from plant based raw material (1) by means of a pretreatment step (2a). The plant based raw material (1) can be treated by means of a hydrolysis and steam explosion treatment in presence of a chemical agent, e.g. $H_2SO_4$, at the pretreatment stage. The lignocellulosic material A (3a) is treated by means of a soaking (2c) after the pretreatment step (2a). The lignocellulosic material B (3b) from the soaking step (2c) is conducted a solid-liquid separation stage (9) which comprises a separation device based on filtration or centrifugal treatment and in which a liquid fraction (11) and a solid fraction (10) are separated before an enzymatic hydrolysis (4), and the solid fraction (10) is conducted into the enzymatic hydrolysis (4) for forming a lignin based material (5). The lignin based material (5) is conducted into a second solid-liquid separation stage (6) which comprises a separation device based on filtration or centrifugal treatment. A soluble carbohydrate containing fraction (8) and a lignin fraction (7) are separated at the solid-liquid separation stage (6). The soluble carbohydrate containing fraction (8) is recovered. A solid cake (7) containing lignin is removed from the solid-liquid separation device and recovered.

Example 4

In this example a lignin fraction and soluble carbohydrate containing fraction are produced from plant based raw material according to a process of FIG. 4.

The lignocellulosic material A (3a) is formed from plant based raw material (1) by means of two pretreatment steps (2a,2b). The plant based raw material (1) can be treated by means of a hydrolysis and steam explosion treatment in presence of a chemical agent, e.g. $H_2SO_4$, at the pretreatment stage. The lignocellulosic material A (3a) is treated by means of a soaking (2c) after the pretreatment steps (2a,2b). The lignocellulosic material B (3b) from the soaking step (2c) is conducted a solid-liquid separation stage (9) which comprises a separation device based on filtration or centrifugal treatment and in which a liquid fraction (11) and a solid fraction (10) are separated before an enzymatic hydrolysis (4). In one embodiment, a part of liquid fraction which comprises soluble carbohydrates may be supplied out and/or recovered between pretreatment steps (2a,2b) or in connection with them. The solid fraction (10) is conducted into the enzymatic hydrolysis (4) for forming a lignin based material (5). The lignin based material (5) is conducted into a second solid-liquid separation stage (6) which comprises a separation device based on filtration or centrifugal treatment. A soluble carbohydrate containing fraction (8) and a lignin fraction (7) are separated at the solid-liquid separation stage (6). The soluble carbohydrate containing fraction (8) is recovered. A solid cake (7) containing lignin is removed from the solid-liquid separation device and recovered.

Example 5

In this example a concentrated liquid (11) and purified solid fraction (10) were produced.

Birch wood chips were pretreated in two-step dilute acid steam explosion process (2a,2b) to dissolve hemicellulose. The formed lignocellulosic material (3a) was mixed with hot water and stirred for a while in a soaking step (2c). Then solid-liquid separation was done with Outotec Larox PF 0.1 pressure filter (9). Filtration area was 0.1 m². Amount of washing water was 1:1 (water:water insoluble solids in the cake) and 3:1. Dry matter of original pretreated biomass was 65%, dry matter of the feed (3b) in the first filtration (9) was 16%, and water insoluble solid content of that was 13%. Water insoluble solid content of the feed was kept constant in filter press while dry matter of slurry was increased due to increased soluble material in slurry. Dry matter of washed cake was about 50%. Composition of the solid fraction, which is further washed in laboratory like in gravimetric washing method to remove all water soluble material, is presented in Table 1. The solid fraction was washed with water in order to remove residue soluble compounds, and after that the properties were determined.

To simulate the increase of concentration when all the washing filtrate of the process and some soluble carbohydrate containing filtrate of first pressing was calculated to use as dilution water of next round, and again after second filtration the washing filtrate and some soluble carbohydrate containing filtrate of pressing was used in dilution of third filtration. In 1:1 washing case about 83% of dilution liquid was soluble carbohydrate containing filtrate and in 3:1 case 48% of dilution liquid was soluble carbohydrate containing filtrate. Washing efficiency was calculated to be 83% (1:1) and 88% (3:1). Finally more than 70 iteration rounds were done. Simulation of the example was done with measured soluble matter content of 18.4% of the pretreated lignocellulosic material. The concentration of soluble matter containing filtrate coming out of the process will reach level of 135 g/l in continuous process with 1:1 washing and 99 g/l with 3:1 washing.

TABLE 1

| Property | Unit | Method | Test 1 | Test 2 |
| --- | --- | --- | --- | --- |
| Acid-insoluble lignin, grav. | % | T-222 | 33.4 | 34.0 |
| Acid-soluble lignin, UV205 | % | T-UM 250 | 1.5 | 1.5 |
| Arabinose, acid hydrolysis, HPAE-PAD | mg/g | SCAN-CM71 | 0.0 | 0.0 |
| Rhamnose, acid hydrolysis, HPAE-PAD | mg/g | SCAN-CM71 | 0.0 | 0.0 |
| Galactose, acid hydrolysis, HPAE-PAD | mg/g | SCAN-CM71 | 0.0 | 0.0 |
| Glucose, acid hydrolysis, HPAE-PAD | mg/g | SCAN-CM71 | 599.3 | 642.7 |
| Xylose, acid hydrolysis, HPAE-PAD | mg/g | SCAN-CM71 | 25.8 | 26.1 |
| Mannose, acid hydrolysis, HPAE-PAD | mg/g | SCAN-CM71 | 0.0 | 0.0 |
| Carbohyrates, acid hydrolysis, HPAE-PAD, total | mg/g | SCAN-CM71 | 625.1 | 668.7 |
| FS5 Length weighted fiber length Lc (1) ISO | mm | Determined by Metso FS5 based on ISO 16065-N or TAPPI T271 | 0.310 | 0.405 |
| FS5 Fiber width | μm | | 23.8 | 19.1 |
| FS5 Fines | % | | 99.5 | 99.1 |
| FS5 Fines (Flakes) | % | | 95.0 | 93.5 |
| FS5 Fines (Fibrils) | % | | 0.0 | 0.0 |
| Population based particle length Lc (n) | mm | | 0.018 | 0.018 |
| Length weighted particle length Lc (1) | mm | | 0.026 | 0.029 |
| Weight weighted particle length Lc (w) | mm | | 0.061 | 0.111 |

TABLE 1-continued

| Property | Unit | Method | Test 1 | Test 2 |
|---|---|---|---|---|
| FS5 Fiber fractions 0-0.2 mm | % | | 99.5 | 99.0 |
| FS5 Fiber fractions 0.2-0.6 mm | % | | 0.4 | 0.8 |
| FS5 Fiber fractions 0.6-1.2 mm | % | | 0.0 | 0.1 |
| FS5 Fiber fractions 1.2-2.0 mm | % | | 0.0 | 0.0 |
| FS5 Fiber fractions 2.0-3.2 mm | % | | 0.0 | 0.0 |
| FS5 Fiber fractions 3.2-7.6 mm | % | | 0.0 | 0.0 |
| Particle width of fraction 0-0.2 mm | μm | | 4.3 | 4.4 |
| Particle width of fraction 0.2-0.6 mm | μm | | 25.0 | 19.0 |
| Particle width of fraction 0.6-1.2 mm | μm | | 11.7 | 15.5 |
| Particle width of fraction 1.2-2.0 mm | μm | | 13.0 | 46.4 |
| Particle with of fraction 2.0-3.2 mm | μm | | | |
| Particle width of fraction 3.2-7.6 mm | μm | | | |
| FS5 Mass fractions 0-0.2 mm | % | | 88.7 | 87.0 |
| FS5 Mass fractions 0.2-0.6 mm | % | | 11.2 | 11.1 |
| FS5 Mass fractions 0.6-1.2 mm | % | | 0.2 | 0.8 |
| FS5 Mass fractions 1.2-2.0 mm | % | | 0.0 | 1.2 |
| FS5 Mass fractions 2.0-3.2 mm | % | | 0.0 | 0.0 |
| FS5 Mass fractions 3.2-7.6 mm | % | | 0.0 | 0.0 |
| FS5 Number of pictures (avg of 3) | pcs | | 639 | 644 |
| FS5 Number of particles (avg of 3) | pcs | | 117076 | 106621 |

Example 6

In this example a liquid fraction (11) and solid fraction (10) were produced.

*Eucalyptus* wood chips were pretreated in one-step auto-hydrolysis and steam explosion process with two different process conditions to dissolve hemicellulose. The formed pretreated lignocellulosic materials were washed with hot water in laboratory to remove most of the water soluble compounds. These remaining, water soluble compound free solids were measured with two different particle size analyzer. The results of Metso FS5 and Coulter LS230 are presented in table 2 'two water insoluble solids of pretreated *eucalyptus* based lignocellulosic materials'. The results may be determined by standards of ISO 16065-N or TAPPI T271.

TABLE 2

| | Unit | Material 1 | Material 2 |
|---|---|---|---|
| FS5 Length weighted fiber length Lc (1) ISO | mm | 0.332 | 0.462 |
| FS5 Fiber width | μm | 16.2 | 21.8 |
| FS5 Fines | % | 98.6 | 86.8 |
| FS5 Fines (Flakes) | % | 94.6 | 66.9 |
| FS5 Fines (Fibrils) | % | 0.0 | 0.0 |
| Population based particle length Lc (n) | mm | 0.018 | 0.026 |

TABLE 2-continued

| | Unit | Material 1 | Material 2 |
|---|---|---|---|
| Length weighted particle length Lc (1) | mm | 0.031 | 0.099 |
| Weight weighted particle length Lc (w) | mm | 0.099 | 0.383 |
| FS5 Fiber fractions 0-0.2 mm | % | 98.6 | 86.8 |
| FS5 Fiber fractions 0.2-0.6 mm | % | 1.3 | 9.6 |
| FS5 Fiber fractions 0.6-1.2 mm | % | 0.1 | 3.6 |
| FS5 Fiber fractions 1.2-2.0 mm | % | 0.0 | 0.0 |
| FS5 Fiber fractions 2.0-3.2 mm | % | 0.0 | 0.0 |
| FS5 Fiber fractions 3.2-7.6 mm | % | 0.0 | 0.0 |
| Particle width of fraction 0-0.2 mm | μm | 5.9 | 7.9 |
| Particle width of fraction 0.2-0.6 mm | μm | 16.3 | 21.1 |
| Particle width of fraction 0.6-1.2 mm | μm | 15.4 | 23.6 |
| Particle width of fraction 1.2-2.0 mm | μm | | |
| Particle with of fraction 2.0-3.2 mm | μm | | |
| Particle width of fraction 3.2-7.6 mm | μm | | |
| FS5 Mass fractions 0-0.2 mm | % | 94.2 | 52.7 |
| FS5 Mass fractions 0.2-0.6 mm | % | 5.7 | 32.3 |
| FS5 Mass fractions 0.6-1.2 mm | % | 0.2 | 15.0 |
| FS5 Mass fractions 1.2-2.0 mm | % | 0.0 | 0.0 |
| FS5 Mass fractions 2.0-3.2 mm | % | 0.0 | 0.0 |
| FS5 Mass fractions 3.2-7.6 mm | % | 0.0 | 0.0 |
| Coulter LS Particle size Mean | μm | 36.5 | 54.8 |
| Coulter LS Particle size Median | μm | 29.9 | 40.8 |
| Coulter LS Particle size Mode | μm | 72.9 | 116.3 |
| Coulter LS Particle size <50 μm | % | 70.6 | 57.0 |
| Coulter LS Particle size <25 μm | % | 43.4 | 32.6 |
| Coulter LS Particle size <10 μm | % | 19.2 | 11.6 |
| Coulter LS Particle size <5 μm | % | 10.5 | 6.5 |
| Coulter LS Particle size <2 μm | % | 4.3 | 2.8 |
| Coulter LS Particle size <1 μm | % | 1.9 | 1.1 |
| Coulter LS Particle size <0.5 μm | % | 0.8 | 0.3 |
| Coulter LS Particle size <0.3 μm | % | 0.4 | 0.1 |

Example 7

In this example, liquid and solid fractions were produced, and their uses in an enzymatic hydrolysis were examined.

Birch wood chips were pretreated in a dilute acid steam explosion process (2a) to dissolve hemicellulose for forming a lignocellulosic material (3a).

The lignocellulosic material (3a) was soaked in a soaking step (2c) for forming a lignocellulosic material (3b). During the soaking, residence time was 24 hours, temperature was about 50° C., and consistency was 28%.

The treated lignocellulosic material (3b) was supplied to a solid-liquid separation device (9). The separation device was a decanter centrifuge in experiments PTB1, PTB2 and PTB3, and the separation device was a pressure filter in experiment PTB4.

The solid samples (PTB1, PTB2, PTB3, PTB4) of the treated biomass were taken after separation stage (9). The results are presented in Table 3.

Further, the solid sample PTB2, taken after separation stage (9), was diluted to level of 15% total solids for an enzymatic hydrolysis (4) in laboratory scale. Mixing of slurry was good, and 5% enzyme/total solids was used in the experiment. Glucose yield after 72 hours was 80%.

Further, the solid sample PTB1, taken after separation stage (9), was diluted. It was observed that PTB1 was not possible to mix in the laboratory experiment at total solids level of 13% or higher, and the enzymatic hydrolysis was not possible to do.

TABLE 3

|  | Unit | PTB1 | PTB2 | PTB3 | PTB4 |
|---|---|---|---|---|---|
| FS5 Length weighted fiber length Lc (1) ISO | mm | 1.399 | 1.665 | 0.500 | 0.764 |
| FS5 Fiber width | μm | 21.0 | 21.4 | 20.0 | 28.1 |
| FS5 Fines | % | 98.3 | 97.8 | 99.2 | 98.7 |
| FS5 Fiber fractions 0-0.2 mm | % | 98.3 | 97.8 | 99.2 | 98.7 |
| FS5 Fiber fractions 0.2-0.6 mm | % | 0.90 | 1.00 | 0.60 | 0.70 |
| FS5 Fiber fractions 0.6-1.2 mm | % | 0.20 | 0.40 | 0.10 | 0.30 |
| FS5 Fiber fractions 1.2-2.0 mm | % | 0.10 | 0.10 | 0.10 | 0.30 |
| FS5 Fiber fractions 2.0-3.2 mm | % | 0.20 | 0.20 | 0.00 | 0.00 |
| FS5 Fiber fractions 3.2-7.6 mm | % | 0.30 | 0.50 | 0.00 | 0.00 |
| FS5 Number of particles | pcs | 114084 | 119703 | 107226 | 120079 |
| FS5 Number of fibers | pcs | 114082 | 119690 | 107219 | 120067 |
| FS5 Fines (Flakes) | % | 93.8 | 90.0 | 96.4 | 92.1 |
| Population based particle length Lc (n) | mm | 0.020 | 0.019 | 0.018 | 0.017 |
| Length weighted particle length Lc (1) | mm | 0.069 | 0.065 | 0.029 | 0.031 |
| Weight weighted particle length Lc (w) | mm | 1.538 | 1.852 | 0.190 | 0.444 |
| Particle width of fraction 0-0.2 mm | μm | 5.2 | 4.3 | 4.4 | 4.3 |
| Particle width of fraction 0.2-0.6 mm | μm | 18.9 | 21.0 | 26.7 | 23.1 |
| Particle width of fraction 0.6-1.2 mm | μm | 18.1 | 14.9 | 24.5 | 20.2 |
| Particle width of fraction 1.2-2.0 mm | μm | 29.2 | 18.1 | 15.4 | 37.5 |
| Particle with of fraction 2.0-3.2 mm | μm | 22.9 | 21.0 | 23.1 | 16.6 |
| Particle width of fraction 3.2-7.6 mm | μm | 24.1 | 26.6 |  | 13.3 |
| FS5 Mass fractions 0-0.2 mm | % | 73.7 | 72.1 | 82.7 | 80.9 |
| FS5 Mass fractions 0.2-0.6 mm | % | 8.4 | 13.0 | 14.1 | 11.9 |
| FS5 Mass fractions 0.6-1.2 mm | % | 3.3 | 1.7 | 2.5 | 2.1 |
| FS5 Mass fractions 1.2-2.0 mm | % | 6.1 | 2.8 | 0.2 | 4.7 |
| FS5 Mass fractions 2.0-3.2 mm | % | 4.6 | 3.5 | 0.5 | 0.3 |
| FS5 Mass fractions 3.2-7.6 mm | % | 3.9 | 6.9 | 0.0 | 0.2 |
| Coulter LS Particle size Mean | μm | 20.3 | 23.8 | 29.4 | 28.6 |
| Coulter LS Particle size Median | μm | 15.9 | 18.4 | 22.1 | 21.1 |
| Coulter LS Particle size Mode | μm | 16.4 | 26.1 | 28.7 | 28.7 |
| Coulter LS Particle size <50 μm | % | 93.8 | 87.7 | 80.2 | 80.4 |
| Coulter LS Particle size <25 μm | % | 69.8 | 62.0 | 54.9 | 56.2 |
| Coulter LS Particle size <10 μm | % | 30.6 | 28.4 | 21.9 | 24.8 |
| Coulter LS Particle size <5 μm | % | 11.6 | 11.9 | 8.4 | 10.2 |
| Coulter LS Particle size <2 m | % | 1.9 | 2.2 | 1.5 | 1.8 |
| Coulter LS Particle size <1 μm | % | 0.1 | 0.1 | 0.1 | 0.1 |
| Coulter LS Particle size <0.5 μm | % | 0.0 | 0.0 | 0.0 | 0.0 |
| Coulter LS Particle size <0.3 μm | % | 0.0 | 0.0 | 0.0 | 0.0 |
| Coulter LS Particle size Spesific surface area | m2/g | 0.61 | 0.59 | 0.48 | 0.53 |
| Brookfield viscosity 10 rpm vane spindle 45° C., 15% total solids | mPas | 19500 | 6233 |  |  |

Example 8

In this example, viscosity of the lignocellulosic material was measured. The lignocellulosic material was according to example 7 after separation (9).

The viscosity was measured at 10, 15 and 20% dry matter content by means of Brookfield viscosity device at 45° C. with 10 rpm and spindle type "Vane". The sample size in the measurement was 300 ml. Sample A had good mixing properties. Sample B had poor mixing properties in mechanically agitated vessel where mixing was done with pitched-blade turbine (45°) type of impellers.

Figure 5:
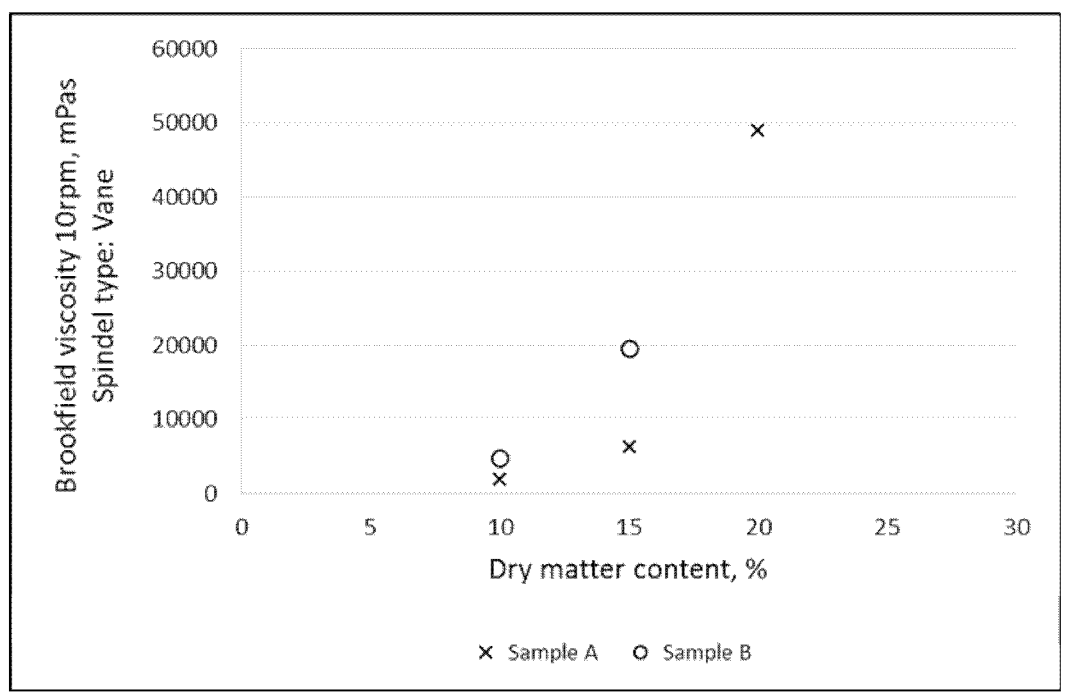
FIG. 5 shows results from a viscosity measurement of the lignocellulosic material according to one method embodiment of the present invention.

The results from the viscosity measurements are presented in FIG. 5. It was observed that the lignocellulosic material with viscosity below 18000 mPas, at 15% dry matter content, is suitable material for an enzymatic hydrolysis and a manufacture of lignin.

The method and apparatus are suitable in different embodiments to be used for producing the most different kinds of lignin and soluble carbohydrate based fractions from different plant based raw materials.

The invention is not limited merely to the example referred to above; instead many variations are possible within the scope of the inventive idea defined by the claims.

The invention claimed is:

1. A method for treating plant based raw material with an enzymatic hydrolysis, in which the plant based raw material is treated to form lignocellulosic material, and the lignocellulosic material or a solid fraction thereof is subjected to the enzymatic hydrolysis, wherein the method comprises:
    treating the plant based raw material in at least one treatment stage by at least one of a physical treatment, chemical treatment, and/or physico-chemical treatment such that the plant based raw material is treated at least by hydrolysis and steam explosion, for forming the lignocellulosic material including over 80% fine solid particles, which are fiber-like or indefinable particles smaller than 0.2 mm, defined by an optical measurement device,
    subjecting the lignocellulosic material or at least one solid fraction of the lignocellulosic material into the enzymatic hydrolysis for forming a lignin based material, and
    subjecting the lignin based material into at least one solid-liquid separation stage after the enzymatic hydrolysis and separating a lignin fraction and a soluble carbohydrate containing fraction.

2. The method according to claim 1, wherein the treatment stage comprises at least one pretreatment step including physical treatment, chemical treatment, physico-chemical treatment, biological treatment, or any combination thereof, wherein the physical treatment includes milling, extrusion, microwave treatment, ultrasound treatment, or freeze treatment, the chemical treatment includes acid treatment, alkaline treatment, ionic liquid treatment, organosolv treatment or ozonolysis, and the physico-chemical treatment includes steam explosion treatment, ammonia fiber explosion treatment, $CO_2$ explosion treatment, liquid hot water treatment or wet oxidation.

3. The method according to claim 1, wherein the plant based raw material is treated using the steam explosion treatment in presence of a chemical agent at the pretreatment step.

4. The method according to claim 3, wherein the chemical agent is a non-alkaline agent.

5. The method according to claim 3, wherein the chemical agent is an acid.

6. The method according to claim 1, wherein the lignocellulosic material is treated by soaking.

7. The method according to claim 1, wherein the lignocellulosic material is diluted for the soaking.

8. The method according to claim 1, wherein the optical measurement device is Metso FS5.

9. The method according to claim 1, wherein the optical measurement device is Coulter LS230.

10. The method according claim 1, wherein the viscosity of the lignocellulosic material is below 18000 mPas at 15% dry matter content, measured by Brookfield viscosity device at 45° C. with 10 rpm and spindel type "Vane".

11. The method according to claim 1, wherein the method comprises more than one solid-liquid separation stage.

12. The method according to claim 1, wherein the lignocellulosic material is subjected to a solid-liquid separation stage in which a liquid fraction and a solid fraction are separated before the enzymatic hydrolysis, and the solid fraction is subjected to the enzymatic hydrolysis.

13. The method according to claim 1, wherein the solid-liquid separation is made using filtration, centrifugal treatment, or a combination thereof.

14. The method according to claim 1, wherein the solid-liquid separation stage comprises a washing in which a displacement washing is carried out with a small amount of clean water in which ratio of washing water to solid is below 6.

15. The method according to claim 1, wherein the plant based raw material comprises wood based material or a mixture comprising wood based material.

16. The method according to claim 1, wherein the soluble carbohydrate containing fraction is used as a source material in a fermentation, hydrolysis, chemical treatment, catalytic treatment, polymerization process, depolymerization process, degradation process, enzymatic treatment, manufacture of binder, manufacture of teed, manufacture of food, or any combination thereof.

17. The method according to claim 1, wherein the lignin fraction is used as a source material in a hydrolysis, polymerization process, depolymerization process, degradation process, chemical treatment, manufacture of a composite material, manufacture of binder, manufacture of feed, manufacture of food, combustion process, or any combination thereof.

18. The method according to claim 1, wherein the lignin based material is used as a source material in a hydrolysis, polymerization process, depolymerization process, degradation process, chemical treatment, manufacture of a composite material, manufacture of binder, manufacture of feed, manufacture of food, combustion process, or any combination thereof.

19. The method according to claim 1, wherein the liquid fraction formed by separating the liquid fraction from the lignocellulosic material before the enzymatic hydrolysis is used as a source material in a fermentation, hydrolysis, chemical treatment, catalytic treatment, polymerization process, depolymerization process, degradation process, enzymatic process, manufacture of binder, manufacture of feed, manufacture of food, or any combination thereof.

20. The method according to claim 1, wherein the solid fraction formed by separating the solid fraction from the lignocellulosic material before the enzymatic hydrolysis is used as a source material in a hydrolysis, polymerization process, depolymerization process, degradation process, chemical treatment, manufacture of a composite material, manufacture of binder, combustion process, or any combination thereof.

21. The method according to claim 1, wherein the liquid mixture comprising a soluble carbohydrate containing fraction and a liquid fraction separated from the lignocellulosic material before the enzymatic hydrolysis is used as a source material in a fermentation, hydrolysis, chemical treatment, catalytic treatment, polymerization process, depolymerization process, degradation process, enzymatic treatment, manufacture of binder, manufacture of feed, manufacture of food, or any combination thereof.

* * * * *

UNITED STATES PATENT AND TRADEMARK OFFICE
CERTIFICATE OF CORRECTION

PATENT NO. : 10,858,673 B2
APPLICATION NO. : 15/545988
DATED : December 8, 2020
INVENTOR(S) : Sami Turunen et al.

It is certified that error appears in the above-identified patent and that said Letters Patent is hereby corrected as shown below:

In the Claims

At Column 26, Line 3 (Claim 16, Line 6), please delete "teed" and insert --feed-- therefor.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*